United States Patent
Kuhn et al.

(10) Patent No.: US 8,275,435 B2
(45) Date of Patent: Sep. 25, 2012

(54) CO-LOCATION OF EMITTERS AND DETECTORS AND METHOD OF OPERATION

(75) Inventors: Jonathan L. Kuhn, Ham Lake, MN (US); Jonathan P. Roberts, Coon Rapids, MN (US); Andrew J. Ries, Lino Lakes, MN (US); James D. Reinke, Maple Grove, MN (US); Jeffrey M. Jelen, New Hope, MN (US); Robert M. Ecker, Lino Lakes, MN (US); Timothy J. Davis, Coon Rapids, MN (US); Can Cinbis, Shoreview, MN (US); Thomas A. Anderson, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 12/690,957

(22) Filed: Jan. 21, 2010

(65) Prior Publication Data
US 2010/0185262 A1 Jul. 22, 2010

Related U.S. Application Data

(60) Provisional application No. 61/146,469, filed on Jan. 22, 2009.

(51) Int. Cl.
*A61B 5/00* (2006.01)
(52) U.S. Cl. .................. 600/323; 600/325
(58) Field of Classification Search .............. 600/310, 600/323–325, 331–333, 339, 341; 607/22
See application file for complete search history.

(56) References Cited

U.S. PATENT DOCUMENTS

| | | | |
|---|---|---|---|
| 3,985,449 | A | 10/1976 | Patrin et al. |
| 4,100,562 | A | 7/1978 | Sugawara et al. |
| 4,202,339 | A | 5/1980 | Wirtzfeld et al. |
| 4,467,807 | A | 8/1984 | Bornzin |
| 4,730,389 | A | 3/1988 | Baudino et al. |

(Continued)

FOREIGN PATENT DOCUMENTS

EP 1764034 3/2007
(Continued)

OTHER PUBLICATIONS (PCT/US2010/021584) PCT Notification of Transmittal of the International Search Report and the Written Opinion of the International Searching Authority, Mailed Apr. 23, 2010, 8 pages.

*Primary Examiner* — Clayton E Laballe
*Assistant Examiner* — Minh Phan
(74) *Attorney, Agent, or Firm* — Michael C. Soldner; Stephen W. Bauer; Evans M. Mburu

(57) ABSTRACT

An implantable medical device having an optical sensor selects the function of modular opto-electronic assemblies included in the optical sensor. Each assembly is provided with at least one light emitting device and at least one light detecting device. A device controller coupled to the optical sensor controls the function of each the assemblies. The controller executes a sensor performance test and selects at least one of the plurality of assemblies to operate as a light emitting assembly in response to a result of the performance test. The controller selects at least one other of the plurality of optical sensor assemblies to operate as a light detecting assembly in response to a result of the performance test.

24 Claims, 5 Drawing Sheets

U.S. PATENT DOCUMENTS

| | | |
|---|---|---|
| 5,010,381 A | 4/1991 | Shiba et al. |
| 5,144,381 A | 9/1992 | Fumyama et al. |
| 5,556,421 A | 9/1996 | Prutchi et al. |
| 5,902,326 A | 5/1999 | Lessar et al. |
| 6,125,290 A | 9/2000 | Miesel et al. |
| 6,198,952 B1 | 3/2001 | Miesel et al. |
| 6,409,675 B1 | 6/2002 | Turcott |
| 6,491,639 B1 | 12/2002 | Turcott |
| 7,013,178 B2 | 3/2006 | Reinke et al. |
| 2004/0176669 A1 | 9/2004 | Colvin et al. |
| 2004/0220629 A1 | 11/2004 | Kamath et al. |
| 2008/0208021 A1 * | 8/2008 | Cinbis et al. .......... 600/324 |

FOREIGN PATENT DOCUMENTS

| | | |
|---|---|---|
| WO | 00/25664 | 5/2000 |
| WO | 2004/098403 | 11/2004 |
| WO | 2008/106597 | 9/2008 |

* cited by examiner

CO-LOCATION OF EMITTERS AND DETECTORS AND METHOD OF OPERATION

CROSS REFERENCE TO RELATED APPLICATION

The present application claims priority and other benefits from U.S. Provisional Patent Application Ser. No. 61/146,469, filed Jan. 22, 2009, entitled "CO-LOCATION OF EMITTERS AND DETECTORS AND METHOD OF OPERATION", incorporated herein by reference in its entirety.

TECHNICAL FIELD

The disclosure relates generally to implantable medical devices and, in particular, to implantable optical sensors for sensing physiological conditions.

BACKGROUND

Implantable medical devices (IMDs) for monitoring a physiological condition or delivering a therapy include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function. One example of an implantable optical sensor used for monitoring blood oxygen saturation is generally disclosed in commonly assigned U.S. Pat. No. 6,198,952 issued to Miesel, hereby incorporated herein by reference in its entirety. Cardiac pacemakers that respond to changes in blood oxygen saturation as measured by an optical sensor are generally disclosed in U.S. Pat. No. 4,202,339 issued to Wirtzfeld and in U.S. Pat. No. 4,467,807 issued to Bornzin, both of which patents are incorporated herein by reference in their entirety. It is desirable to provide methods for manufacturing and implementing implantable optical sensors in a low cost and time-efficient manner that promotes ease of assembly with an associated IMD.

DETAILED DESCRIPTION

Figure 1:
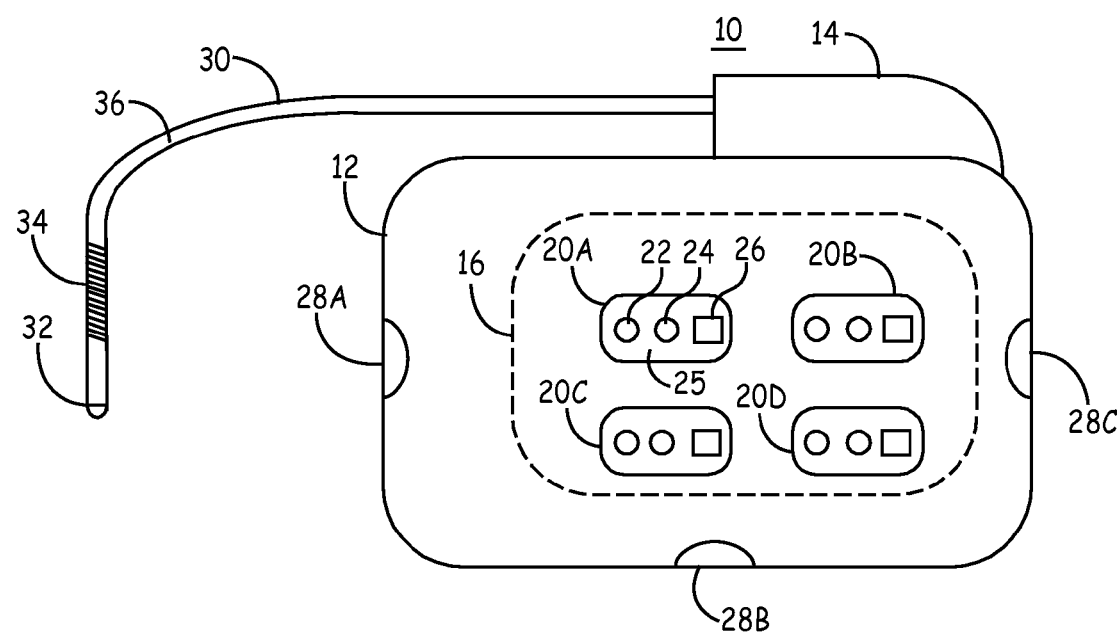
FIG. 1 is a diagram of one embodiment an IMD.

In the following description, references are made to illustrative embodiments. It is understood that other embodiments may be utilized without departing from the scope of the invention. For purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, the term "opto-electronic device", also referred to herein as "opto-electronic component", refers to any electrical circuit component capable of emitting light in response to an applied voltage or current or emitting current in response to exposure to light, including for example light emitting diodes (LEDs), vertical cavity surface emitting lasers (VCSELs), photoresistors or light dependent resistors, photodiodes, phototransistors, photovoltaic cells, or charge-coupled devices.

FIG. 1 is a diagram of one embodiment an IMD 10. IMD 10 is shown as a subcutaneous implantable cardioverter defibrillator (ICD) including an array of subcutaneous electrodes 28A, 28B, and 28C, referred to collectively as electrodes 28, which are incorporated along housing 12 of IMD 10. Housing 12 encloses circuitry (not shown) within IMD 10. Enclosed circuitry is coupled to electrodes 28 and other electrodes and sensors to be described herein via appropriate conductors and feedthroughs not shown in detail in FIG. 1. IMD 10 may include a connector block 14 for receiving an electrical lead 30 carrying electrodes 32 and 34 along a lead body 36. Any of electrodes 28, tip electrode 32 and coil electrode 34 may be used for sensing electrocardiogram (ECG) signals. Coil electrode 34 is a high-voltage electrode used to deliver high-voltage cardioversion/defibrillation shocks to a patient's heart in response to detecting a shockable arrhythmia from sensed ECG signals. In various embodiments, IMD 10 may include any combination of electrodes carried by one or more leads and/or incorporated in housing 12. Lead 30 may be a subcutaneous lead tunneled to a location outside the thoracic cavity. In alternative embodiments, transvenous leads or epicardial leads may be coupled to IMD 10.

IMD 10 includes an optical sensor 16. Optical sensor 16 is provided with modular sensor assemblies 20A, 20B, 20C and 20D, referred to collectively as assemblies 20. While four assemblies 20 are shown arranged in a generally square configuration in FIG. 1, two or more assemblies may be included in a medical device. The assemblies may be arranged in any linear, circular or other geometric or random arrangement relative to each other. Furthermore, while all of assemblies 20 are shown arranged along a single side of IMD housing 12, it is recognized that assemblies 20 may be arranged on any side or edge of IMD 10, for example along opposing sides, and may alternatively or additionally be positioned along connector block 14, carried by a lead body or even located on separate devices capable of communicating with each other. As will be described herein, the functionality of each assembly is controlled by IMD 10. For example, assembly 20A may be controlled to emit light as a part of a light emitting portion of sensor 16, and assembly 20B may be selected to detect light as a part of a light detecting portion of sensor 16, or vice versa.

The assemblies 20 are shown arranged in a "side-by-side" manner in which an assembly detecting light will receive light that has been emitted by the sensor 16 and scattered by tissue back to the optical sensor. Light transmitted through the tissue and not scattered back to one of assemblies 20 will not be detected. In other embodiments, the assemblies 20 may be arranged to face each other, or positioned at any other angle relative to each other, such that at least some light emitted by one assembly may be transmitted through tissue to reach a light detecting device of another assembly.

Each of assemblies 20 are shown to include one light detecting device 26 and two light emitting devices 22 and 24. In various embodiments, assemblies 20 may include two or more opto-electronic devices with at least one device capable of emitting light and at least one device capable of detecting light. Two or more light emitting devices may be provided for emitting light at separate wavelengths. In one embodiment light detecting device 26 is provided as a photodetector and light emitting devices 22 and 24 are provided as LEDs, for example an LED emitting red light and another LED emitting infrared light.

However, embodiments described herein are not limited to any particular number or arrangement of light emitting and light detecting devices as long as each optical sensor assembly 20 includes at least one device capable of emitting and one capable of detection. In this way, assemblies 20 are provided as modular assemblies each including the necessary opto-electronic components to allow the assembly to operate as either a light emitting portion of optical sensor 16 or a light detecting portion of optical sensor 16. In some embodiments, these modular assemblies 20 do not include optical insulation between any of the opto-electronic devices within an individual assembly 20, but do include optical insulation surrounding the opto-electronic devices, as generally described in the U.S. patent application Ser. No. 12/116,705 and U.S. patent application Ser. No. 11/955,039, both of which are incorporated herein by reference in their entireties. The opto-electronic devices 22, 24 and 26 are referred to as "co-located" devices in that they are located within a single modular assembly 20, which can be manufactured as an assembled unit prior to being installed in the IMD. For example device 22, 24 and 26 may be positioned along a single circuit board and positioned along a common window.

In one embodiment, during patient monitoring, sensor 16 is operable for sensing an optical physiological signal when a given assembly is operating as either an emitting portion or a detecting portion but not both emitting and detecting at any given time. In other embodiments, which include optical insulation between light emitting device and light detection devices, a single module may be selected to operate simultaneously as both a light emitting portion and a light detecting portion of the optical sensor. An exception to simultaneous light emission and detection by a single assembly 20 may occur during assembly performance tests as will be described herein. For example, drift or fluctuation in a light emitting device output may be monitored by using a co-located detecting device for taking a reference measurement. Simultaneous light emission and detection by a single assembly would otherwise prevent sensor 16 from operating properly for patient monitoring. It is recognized that a single assembly 20 may be controlled by control circuitry within IMD 10 to operate as a light emitting portion at certain times and as a light detecting portion at other times.

Each assembly 20 is positioned adjacent a window 25 formed in IMD housing 12 through which light may be emitted or detected. While each assembly 20 is shown positioned along a separate window 25, a single window may be formed in IMD housing 12 through which all of assemblies 20 are exposed to enable light emission and detection. When a single window is used, optical barriers may be required between assemblies 20. Light emitted by one or both of light emitting device 22 and light emitting device 24 of at least one assembly 20 is scattered by a tissue volume adjacent to sensor 16 and detected by at least one light detecting device 26. The light detecting device(s) 26 generates a current signal used by the IMD 10 to detect a patient condition.

As will be described herein, a controller within IMD 10 controls assemblies 20 during optical sensor performance tests. The IMD controller then determines based at least in part on the performance tests, which assemblies 20 will be selected to operate as light emitting portions and which assemblies 20 will be selected to operate as light detecting portions during optical sensing for patient monitoring based on the performance test results.

Implementation of optical sensor 16 using multiple modular assemblies 20, with the functionality of each modular assembly 20 determined by the IMD, promotes low cost, time efficient manufacturing of optical sensor 16. Each assembly 20 can be manufactured to have identical components, with the functionality of each assembly 20 determined by the IMD. The capability of selecting the functionality of each modular assembly 20 further enables IMD 10 to operate using the optimal optical sensing configuration available. For example, if one of the assemblies 20 is highly susceptible to ambient light due to the position of IMD 10 after implantation, that assembly may be selected to operate as a light emitting portion instead of a light detecting portion or not selected to operate at all.

Other factors that may affect the functional selection of the assemblies 20 include dysfunction of any optoelectronic devices, sensor signal level, and sensor signal response to physiological variables. These and other factors may change over time causing the optimal sensing configuration to change over time. Implementation of modular assemblies 20 allows the optimal sensing configuration to be identified and assembly functionality to be selected at any given time according to changing conditions.

Figure 2:
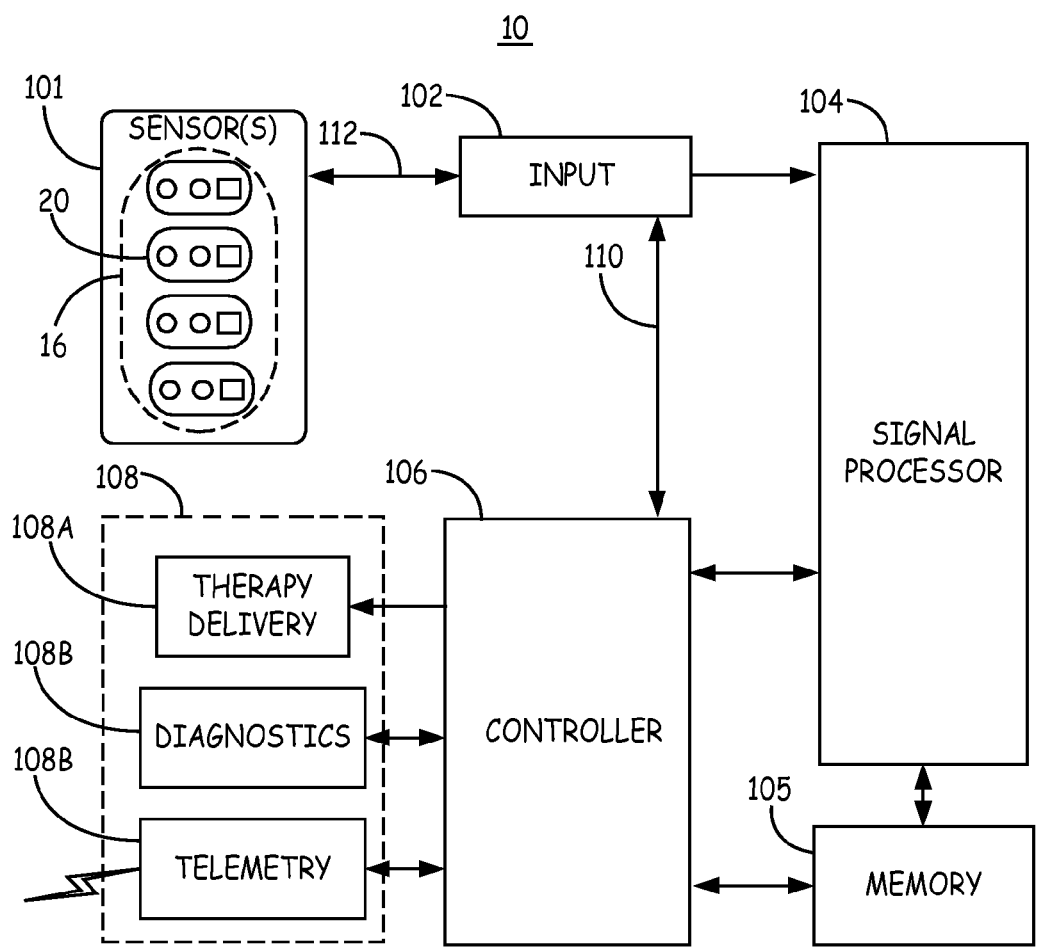
FIG. 2 is a functional block diagram of the IMD of FIG. 1 according to one embodiment.

FIG. 2 is a functional block diagram of IMD 10 according to one embodiment. IMD 10 includes a sensor module 101, an input module 102, signal processor 104, memory 105, controller 106, and output module 108. Sensor module 101 is provided with at least an optical sensor 16 including multiple sensor assemblies 20 as described in conjunction with FIG. 1. Sensor module 101 may include additional sensors used by IMD 10 for detecting patient conditions and making therapy delivery decisions. In various embodiments, sensor module 101 may include an activity sensor, a posture sensor, ECG sensing electrodes, pressure sensors, motion sensors, or other physiological sensors.

Input module 102 receives sensor signal(s) when enabled for sensing by controller 106 by control/status line 110. Input module 102 may perform pre-processing signal conditioning, such as analog filtering. Input module 102 selects the functionality of assemblies 20 via control bus 112 under the control of controller 106. Input module 102 provides optical sensor signals to signal processor 104. Input module 102 may additionally provide other sensor signals to processor 104 and/or controller 106 for use in monitoring physiological signals and detecting physiological events.

The methods employed for enabling an opto-electronic device of a selected assembly to function as a light detecting device or as a light emitting device will depend in part on the overall medical device architecture and hardware, firmware, and software employed. In one embodiment, selection of a light detecting device to operate as a light detecting portion of the optical sensor includes providing a control signal on control bus 112 for coupling the light detecting device to a photo-integrator which converts the device-generated current to a voltage signal which is then provided to an A/D converter. Selection of a light emitting device to operate as a light emitting portion of the optical sensor 16 generally includes coupling the device to a drive signal source to activate the device to emit light. One example of a bus system for controlling a device is generally disclosed in U.S. Pat. No. 7,013,178 (Reinke, et al.), hereby incorporated herein by reference in its entirety.

Processor 104 receives the signals from optical sensor 16 and performs signal processing to provide controller 106 with signals useful in monitoring a patient condition and appropriately control output module 108. Processor 104 may be a digital signal processor (DSP), analog processor or a combination of both analog and digital processors.

Controller 106 controls input module 102 to select the functionality of assemblies 20 during a performance test. IMD 10 executes an optical sensor performance test to evaluate optical sensor signals obtained during different assembly functionality configurations. The physical configuration of assemblies 20 within sensor 16 or across one or more devices is determined at the time of manufacture. However, the functional configuration of the assemblies 20 is controlled by IMD controller 106. Controller 106 controls the selection of each assembly to function as either a light emitting portion or a light detecting portion (or neither or both light emitting and light detecting in some embodiments) in a functional configuration of sensor 16 used for patient monitoring.

During a performance test, assembly functionality is controlled and optical sensor signals are provided to processor 104. Processor 104 provides controller 106 signal data from which controller 106 determines the optimal assembly functionality configuration for optical sensing. The optimal sensing configuration is then selected by input module 102 under the control of controller 106 during episodes in which optical sensor 16 is enabled for monitoring physiological signals.

Signal data may be stored in memory 105 by processor 104 and retrieved by controller 106 for use in determining an optimal functional configuration of assemblies 20. Algorithms for a performance test and other IMD functions may also be stored in memory 105 and retrieved by controller 106.

During normal IMD operation, controller 106 analyzes processed sensor signals provided by processor 104 to detect physiological events or a patient condition. Controller 106 can determine which emitting and detecting configurations of assemblies 20 provide signals with the highest signal-to-noise ratio and acceptable signal level and may select assemblies to operate to provide redundant signals to promote accurate detection. Alternatively, controller 106 may select emitting and detecting configurations of assemblies 20 that minimize energy demands while providing a reliable optical sensor signal for use in patient monitoring. The ability to select the functionality of assemblies 20 over time allows IMD 10 to accommodate situations in which signal characteristics change over time, for example due to shifting of IMD 10 or changes in adjacent tissue composition such as increased tissue encapsulation. By periodically repeating performance tests, controller 106 can select the optimal assembly functionality configuration as it changes over time.

Controller 106 uses the digitally processed signals to make decisions regarding therapy delivery by therapy delivery module 108A, for determining and storing a diagnostic output (such as a detected physiological event) in diagnostics module 108B, and/or for selecting data to be transmitted by telemetry module 108C. Controller 106 may employ a microprocessor and associated memory 105 or digital state machines for timing sensing and therapy delivery functions and controlling other device operations in accordance with a programmed operating mode. The signal acquisition, processing and analysis methods described herein and selection of optical sensor assemblies may be implemented using any combination of software, hardware, and/or firmware.

Therapy delivery module 108A may provide electrical stimulation therapy or drug delivery therapy. In one embodiment, therapy delivery module 108A includes a pulse generator for generating low-voltage pacing pulses, e.g., for bradycardia pacing, cardiac resynchronization therapy, and anti-tachycardia pacing. Therapy delivery module 108A may further include high-voltage circuitry for generating high-voltage cardioversion/defibrillation shocks. Therapy delivery unit 108A includes therapy delivery elements (not explicitly shown) such as electrodes, catheters, drug delivery ports or the like for administering a therapy.

Diagnostics module 108B may be used to detect a physiological event or patient condition using any available sensor signals or other data acquired by the IMD and store data relating to the analysis of processed signals. Stored data may be made available to a clinician through telemetry by telemetry module 108C or accessed by controller 106 for making therapy decisions.

Figure 3:
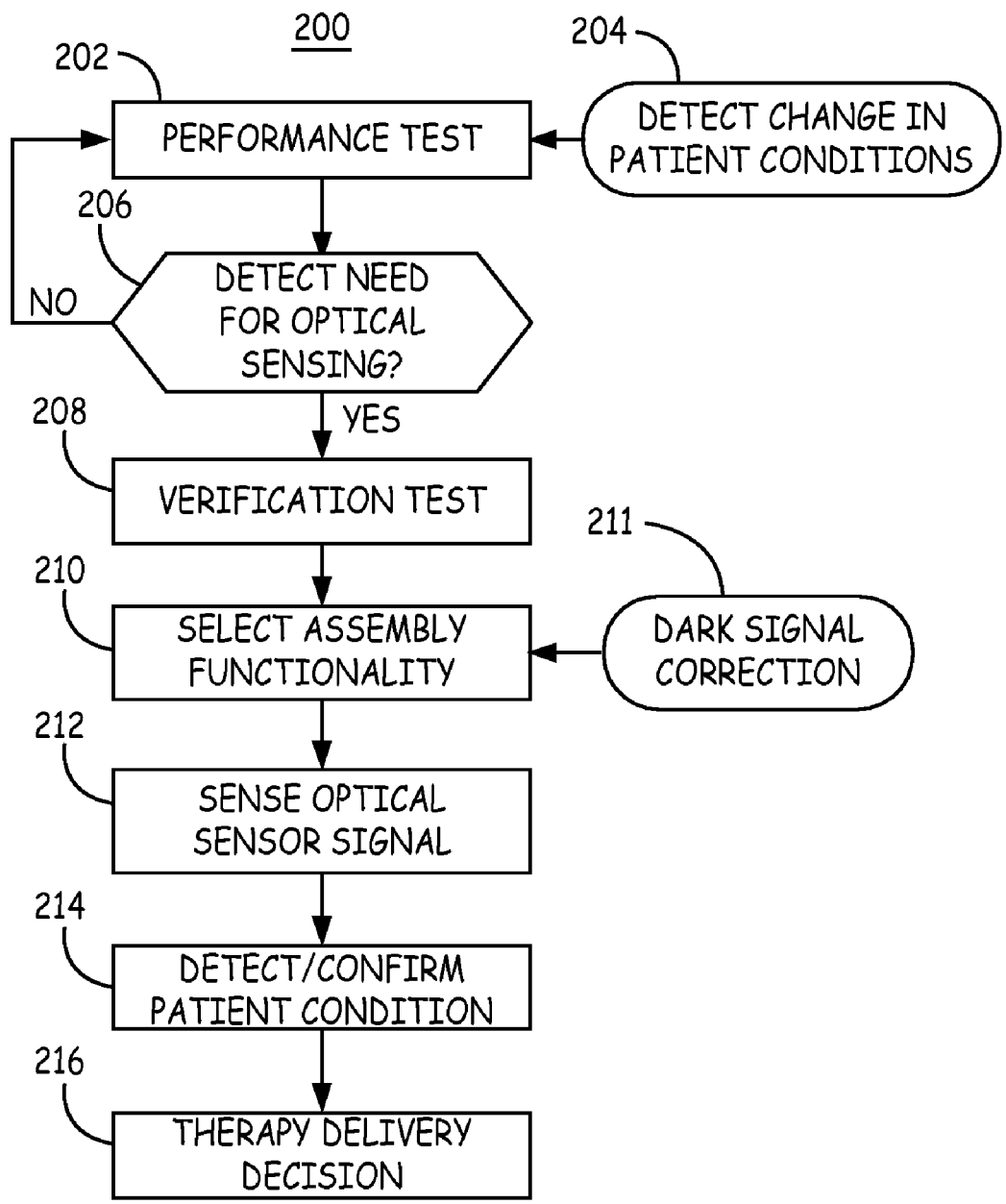
FIG. 3 is a flow chart of one method for selecting the functionality of modular optical sensor assemblies.

FIG. 3 is a flow chart of one method 200 for selecting the functionality of modular optical sensor assemblies. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software, firmware and/or hardware to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The IMD 10 executes an optical sensor performance test at block 202. The performance test may be performed upon implantation of the IMD, upon receiving an external command, or on a scheduled periodic basis. Additionally or alternatively, the performance test 202 may be executed in response to detecting a change in a patient condition, as indicated by block 204. The IMD controller may detect a change in a patient condition based on signals received from other physiological sensors such as an activity sensor, a posture sensor, or ECG electrodes.

The optimal assembly functionality configuration may change if a patient condition changes. For example, a change in patient posture or activity may cause an assembly to be shifted against bone or other tissue that alters the optical sensor signal. A change in patient position or activity may cause an assembly to be more susceptible to ambient light. Accordingly, the performance test may be performed at block 202 in response to other sensor signals to identify the optimal functional configuration of the assemblies for the current patient conditions. Furthermore, it may be desirable to identify functional assembly configurations that are least sensitive to posture changes, activity changes, or other changing conditions.

A change in a patient condition may also be predictive of the need for using the optical sensor. For example, an increased ventricular rate, premature ventricular contractions, or other cardiac events known to precede an arrhythmia may be detected from a sensed ECG signal. When events predictive of an arrhythmia are detected, the IMD controller may anticipate the need to use the optical sensor for confirming or detecting an arrhythmia, alone or in combination with other sensor signals such as the ECG signals. Accordingly, the controller may execute a performance test at block 202 to identify the optimal sensing configuration prior to enabling the optical sensor for arrhythmia detection purposes. The performance test executed at block 202 will be described in detail in conjunction with the flow charts of FIGS. 4 and 5.

The performance test may also be executed at block 202 in response to detecting a change in the optical sensor signal itself. In some embodiments, continuous or periodic optical sensing may be performed for monitoring a patient condition. A change in the optical sensor signal during patient monitoring may indicate an improperly functioning opto-electronic device, a change in ambient light conditions, a change in adjacent tissue composition, or other changes in the sensor operating environment. Changes in the optical sensor signal that warrant a performance test may include a change in the signal-to-noise ratio, a change in the signal baseline, a change in the peak-to-peak amplitude, a signal exceeding an acceptable signal range, or other changes that are unexpected or non-physiological. Unexpected or non-physiological changes may be detected based on predetermined thresholds or based on input received from other sensor signals that do not corroborate with the change observed in the optical sensor signal.

During the performance test, the IMD stores data that enables the IMD controller to select the functionality of the sensor assemblies to achieve an optimal light emitting and light sensing configuration. The optimal sensor configuration may be selected immediately and the optical sensor enabled for sensing upon completion of the performance test. In other embodiments, the optimal configuration may be stored for later selection during optical sensing on a periodic or triggered basis. For example, an optical sensor may be enabled for sensing once per minute, once per hour, daily, or on another periodic basis. Alternatively, the optical sensor may be activated in response to detecting a physiological event or patient condition based on other sensor signals. The optical sensor signal is then activated to provide additional data for the IMD controller to use in detecting or confirming an event or patient condition. For example, an arrhythmia may be detected based on subcutaneous ECG signals. The optical sensor may be activated to generate a signal corresponding to modulation of the optical signals due to changes in tissue perfusion, which can then be analyzed for confirming the detected arrhythmia.

At block 206, the IMD controller detects a need to enable the optical sensor for patient monitoring. If it is not time to enable the sensor, method 200 waits until it is time to repeat the performance test at block 202 or until a need to enable the optical sensor for patient monitoring is detected. Depending on the particular sensing application, verification testing may optionally be performed at block 208 to verify that previous performance test results are still valid. A verification test may include any portion or all of the testing executed during the performance test at block 202. Any verification testing executed at block 208 will depend in part on the time elapsed since the last performance test, the confidence in the results of the test, the urgency of the need for optical sensing and the time required for performing the testing. In some embodiments, verification test 208 will include a short verification test, for example to verify the operability of the optimal sensing configuration identified during the performance test and/or verify that the sensor signal is still within an acceptable signal range. If the optimal sensor signal is needed urgently, for example to confirm a life-threatening arrhythmia, additional verification testing may not be performed.

At block 210, the functionality of each modular assembly within the optical sensor is selected based on the performance test results and verification test results if available. The functionality of each assembly determines the optical sensing configuration. An assembly can be either enabled or disabled. Each assembly that is enabled will be selected to function as either a light emitting portion of the optical sensor or as a light detecting portion of the optical sensor. One or more assemblies may be selected to operate as light emitters and one or more assemblies may be selected to operate as light detectors. In some embodiments, more than one assembly may be selected to emit light sequentially with a single assembly detecting light to provide two different, time-divided, signals. In other embodiments, multiple assemblies may be selected to function as light emitters simultaneously to provide adequate signal strength. In still other embodiments, two different pairs of assemblies may be selected to operate in light emitting and detecting pairs in a sequential manner to provide time-divided, redundant signals.

It is recognized that an optimal configuration selected at block 210 may include a variety of combinations of the available assemblies. Any number of assemblies may be selected to operate as light emitters as long as at least one assembly is selected to operate as a light detector. Likewise, any number of assemblies may be selected to operate as light detectors as long as at least one assembly is selected to operate as a light emitter. When multiple emitters and/or detectors are selected, the emitters and detectors may be selected in any simultaneous or sequential combinations desired to achieve acceptable signal strength, signal-to-noise ratio, signal content, and/or signal redundancy.

The selection of the function configuration of the assemblies at block 210 may take into account a previously determined dark signal for each assembly as indicated by block 211. A dark signal is the signal generated by a light detecting device in the absence of light and is due to leakage currents in the assembly and sensor electronics. A dark signal may be determined for each assembly at the time of manufacture, and may be determined at body temperature. The dark signal produces an offset in the signal baseline. A correction may be made for the dark signal for a selected configuration. All else being equal, an assembly having a greater dark signal than other assemblies may be considered less optimal for functioning as a light detector. However, other factors, such as ambient light susceptibility, overall signal strength, etc. will be taken into account in selecting the optimal functional configuration.

The physical configuration of the assemblies may preclude the selection of certain combinations of light emitters and light detectors. For example, the physical distance or relative orientation between two assemblies may prevent those assemblies from producing an acceptable signal when selected together as a light emitting and light detecting pair. Accordingly, certain combinations of assemblies may be identified and stored in IMD memory as non-selectable configurations. Non-selectable configurations may be stored in the device at the time of manufacture and/or programmable by a user. These non-selectable configurations may be eliminated from the performance test at block 202 and/or eliminated from the available configurations selected from at block 210.

After selecting the optimal functional configuration, the optical sensor signal is sensed at block 212 and used by the IMD to detect or confirm a physiological event or patient condition at block 214. The detected patient condition or event may be used at block 216 to make therapy delivery decisions. Therapy delivery decisions may include delivering, withholding, or adjusting a therapy. In one embodiment, the optical sensor signal is used to confirm an arrhythmia detection and the need to deliver a cardioversion/defibrillation shock. The optical sensor signal may further be used in detecting a response to a delivered therapy, e.g., confirming success of an arrhythmia therapy and that no further therapies are needed.

Figure 4:
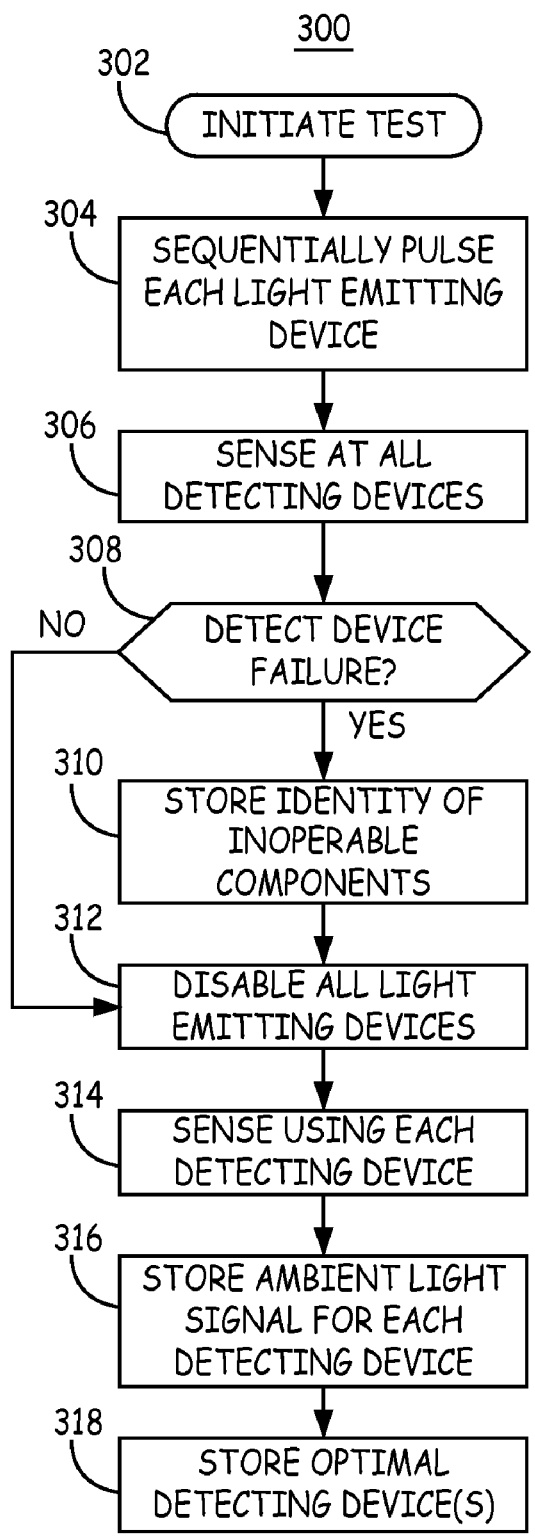
FIGS. 4 and 5 are flow charts of an optical sensor performance test according to one embodiment.
Figure 5:
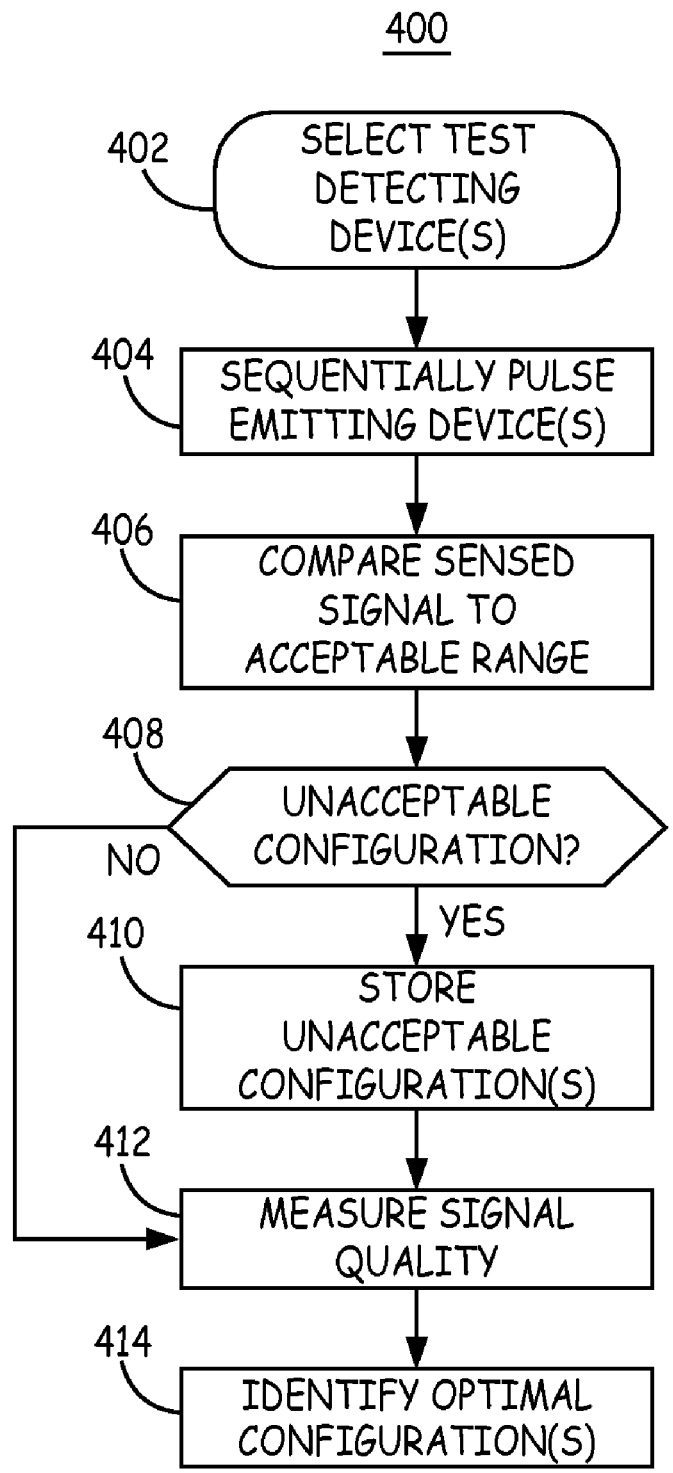

FIGS. 4 and 5 are flow charts of an optical sensor performance test according to one embodiment. Method 300 of FIG. 4 is performed to test the operability of the opto-electronic devices and test for ambient light effects. In FIG. 5, method 400 includes signal quality tests for identifying the optimal sensing configuration from the operable opto-electronic devices. Both methods 300 and 400 may be executed at performance test block 202 of FIG. 3. Any portion of methods 300 and 400 may be executed during verification testing at block 208 of FIG. 3.

Referring to FIG. 4, the performance test is initiated at block 302 in response to a scheduled test time, another sensor signal, a test command provided by a user, or a change in the optical sensor signal. At block 304, each of the opto-electronic devices included in the modular assemblies is pulsed to emit light. The light emitting devices may be pulsed in a sequential manner. All of the opto-electronic devices capable of detecting light are selected at block 306, including the light detecting device(s) co-located with the light emitting device being pulsed at any given time. It is recognized that in some embodiments, an opto-electronic device may be capable of both emitting and detecting light and may therefore be tested in both functions during method 300.

At block 308, the sensor signals from each of the selected light detecting devices are processed and analyzed to determine if any opto-electronic devices are not operating properly. The light detecting device(s) co-located with a pulsed light emitting device is expected to produce a saturated signal in the embodiments having no optical insulation present between co-located opto-electronic components within a given assembly. This saturated signal is evidence that both the pulsed light emitting device and the co-located light detecting device(s) are operating properly. If the light detecting device (s) co-located with a pulsed light emitting device do not produce a saturated signal, but other light detecting devices included in other assemblies produce a signal corresponding to the wavelength of the pulsed light emitting device, the co-located light detecting device is not operating properly and the light emitting device is operable. If no light detecting devices produce a signal corresponding to the wavelength of the pulsed light emitting device, the light emitting device is not operating properly.

Saturation may be defined for a given application based on the operating parameters for the application. At predefined operating parameters, such as the drive current applied to the light emitting devices and the gain and integration time applied to the detecting device signal, saturation of the A/D converter can be achieved. A saturation detection threshold may be set as a value at or near the maximum range of an A/D converter when the light detecting device signal is expected to cover that range for known operating parameters. In other embodiments, saturation may be defined as a signal threshold level assumed to indicate proper operation of the light emitting device.

In other embodiments, light emitting devices emitting light at the same wavelength may be pulsed to emit light simultaneously with all light detecting devices selected to sense. For example, when each assembly includes a red LED and an infrared LED as described in the illustrative embodiment of FIG. 1, all of the red LEDs may be pulsed simultaneously. Each assembly producing a saturated signal is an assembly in which both the red LED and the co-located light detecting device are operating properly. This test may then be repeated for the infrared LEDs. If any assembly does not produce a saturated signal, additional operability testing may be performed to determine if the light emitting device or the light detecting device or both are inoperable.

If all assemblies are determined to be fully operable, testing proceeds to block 312 to evaluate the effect of ambient light. If a device or assembly is determined to be inoperable, as indicated at block 308, the identity of the device or assembly is stored as an inoperable component at block 310. Inoperable assemblies will be stored as non-selectable assemblies. If any opto-electronic component within an assembly is operating and other co-located components are not operable, the operable component may still be identified as a selectable component.

After identifying the operable components, ambient light testing is performed. Ambient light testing is performed by disabling all light emitting devices at block 312 and sensing at block 314 using each light detecting device except those determined to be inoperable. The individual light detecting device signals are compared to determine the light detecting device(s) with a minimum signal. The minimum signal indicates the associated light detecting device is receiving the least ambient light. If an ambient light signal exceeds a predetermined threshold, the associated light detecting device may be designated as a device that is not selectable for optimal sensing. The ambient light signal may be stored for each of the light detecting devices at block 316.

The assembly having the lowest ambient light signal may be identified and stored at block 318 as the optimal assembly for light detection. However, it is recognized that the final assembly functionality configuration selected for patient monitoring may not include the light detecting device having the minimum ambient light signal since other factors, such as signal strength, signal-to-noise ratio, peak-to-peak signal variation, etc., may contribute to determining the optimal sensing configuration.

The performance test continues with method 400 of FIG. 5. Method 400 includes selecting test light detecting devices at block 402. Initially, only the light detecting device identified as the optimal device in method 300, i.e., having the minimum ambient light signal, may be selected at block 402. Alternatively, any number of light detecting devices determined as operable and having the lowest ambient light signals, or ambient light signals below a predetermined threshold, may be selected for additional testing in method 400.

Using an initially selected light detecting device, light emitting devices that are not co-located with the selected light detecting device are sequentially pulsed at block 404. The sensed signal is compared to an acceptable signal range at block 406. If the sensed signal is outside the acceptable signal range, the light detecting and light emitting device combination is unacceptable, as determined at block 406. Unacceptable signal configurations are stored at block 410. Alternatively, each configuration found to produce acceptable signal strength may be stored as an acceptable signal configuration.

If no combination of a single light emitting device and a single light detecting device provides a signal large enough to fall within the acceptable signal range, the light emitting devices may be selected two (or more) at a time simultaneously with a test light detecting device until an acceptable signal strength is obtained.

For each acceptable test signal configuration, additional signal quality measures may be made at block 412. Signal quality measurements may include determining the signal strength (peak or mean signal amplitude), the signal-to-noise ratio, the peak-to-peak signal variation, or other signal characteristics. Desirable signal characteristics will likely depend on the particular sensing application. For example, in some embodiments, signal variation with respiration may be desirable to allow respiration monitoring. In other embodiments, signal variation due to respiration may be considered artifact. For example, a signal producing the maximum variation with cardiac pulsatility and minimum respiration artifact may be desired.

Based on the results of the device operability tests and ambient light signal measurements of method 300 and the signal acceptability and signal quality tests of method 400, the IMD controller identifies an optimal sensing configuration at block 414. The optimal sensing configuration may be a single configuration of one or more light emitting devices operating simultaneously with one or more light detecting devices. At other times or in other embodiments, the optimal sensing configuration may be determined to include two or more sensing configurations operating sequentially to provide multiple signals. Multiple sensing configurations may be selected to allow configurations producing different signal content to be sensed or to allow redundant signals to be sensed to improve confidence in detection algorithms using the optical sensor signal.

Thus, an implantable medical device having an optical sensor and associated method for use have been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
an optical sensor to generate a signal responsive to a physiological condition, the optical sensor comprising a plurality of modular assemblies, each assembly comprising at least one light emitting device co-located with at least one light detecting device; and
a controller coupled to the optical sensor and controlling the function of each the plurality of modular assemblies, the controller executing a sensor performance test and selecting at least one of the plurality of assemblies to operate as a light emitting assembly in response to a result of the performance test, the controller selecting at least one other of the plurality of optical sensor assemblies to operate as a light detecting assembly in response to the result of the performance test.

2. The device of claim 1 wherein at least one of the plurality of assemblies comprises a plurality of light emitting devices emitting light at separate wavelengths.

3. The device of claim 2 further comprising a physiological sensor, the controller receiving a signal from the physiological sensor and executing at least a portion of the performance test in response to the received signal.

4. The device of claim 3 wherein the controller predicts a need to operate the optical sensor at a future time in response to the received signal.

5. The device of claim 3 wherein the controller determines a patient condition in response to the physiological signal and determines a baseline signal for the optical sensor corresponding to a patient condition.

6. The device of claim 1 wherein the controller enables the at least one light detecting device in each of a plurality of the sensor assemblies during the performance test, simultaneously enables the at least one light emitting device, measures a signal from each of the selected light detecting devices, and determines if the selected light emitting device and the co-located selected light detecting device are operating in response to the detected signals.

7. The device of claim 6 wherein the controller enables the at least one light detecting device in each of a plurality of the sensor assemblies, disabling all of the light emitting devices in the optical sensor, and measures an ambient light signal from each of the enabled light detecting devices.

8. The device of claim 7 wherein the controller selects the light detecting assembly in response to the ambient light signal measurements.

9. The device of claim 6 wherein the controller receives a signal from a test light detecting device, sequentially enables each of a plurality of light emitting devices not co-located with the test light detecting device and determined to be operating during the performance test, and compares a signal generated by the test light detecting device to an acceptable signal range,
wherein the controller selects the light emitting assembly and the light detecting assembly in response to the comparison to the acceptable signal range.

10. The device of claim 9 wherein the controller simultaneously enables at least two of the plurality of light emitting devices determined to be operating during the performance test in response to the light detecting device signal not falling within the acceptable signal range during enabling of a single one of the plurality of light emitting devices.

11. The device of claim 9 wherein the controller determines a peak-to-peak amplitude of the light detecting device signal and selects the light emitting assembly and the light detecting assembly in response to the peak-to-peak amplitude.

12. The device of claim 1, wherein the controller selects at least two of the plurality of assemblies to alternate as light emitting assemblies.

13. A method for use in an implantable medical device having an optical sensor comprising a plurality of modular assemblies, each assembly comprising at least one light emitting device co-located with at least one light detecting device, the method comprising:
executing an optical sensor performance test;
selecting at least one of the plurality of assemblies to operate as a light emitting assembly in response to a result of the performance test; and
selecting at least one other of the plurality of optical sensor assemblies to operate as a light detecting assembly in response to the result of the performance test.

14. The method of claim 13 wherein executing the performance test comprises:
enabling the at least one light detecting device in each of a plurality of the sensor assemblies;
simultaneously enabling the at least one light emitting device;
detecting a signal from each of the enabled light detecting devices; and determining if the light emitting device and the light detecting device co-located with the light emitting device are operating in response to the detected signals.

15. The method of claim 14 wherein executing the performance test further comprises:
enabling the at least one light detecting device in each of a plurality of the sensor assemblies;
disabling all of the light emitting devices in the optical sensor; and
measuring an ambient light signal from each of the enabled light detecting devices.

16. The method of claim 15 further comprising the selecting the light detecting assembly in response to the ambient light signal measurements.

17. The method of claim 16, further comprising selecting at least two of the plurality of assemblies to alternate as light emitting assemblies.

18. The method of claim 14, further comprising:
receiving a signal from a test light detecting device;
sequentially enabling each of a plurality of light emitting devices not co-located with the test light detecting device and determined to be operating during the performance test;
comparing a signal generated by the test light detecting device to an acceptable signal range; and
selecting the light emitting assembly and the light detecting assembly at least in part in response to the comparison to the acceptable signal range.

19. The method of claim 18 further comprising enabling at least two of the plurality of light emitting devices determined to be operable during the performance test in response to the light detecting device signal not falling within the acceptable signal range during enabling of a single one of the plurality of light emitting devices.

20. The method of claim 18 further comprising:
determining a peak-to-peak amplitude of the light detecting device signal; and
selecting the light emitting assembly and the light detecting assembly in response to the peak-to-peak amplitude.

21. The method of claim 18 further comprising:
sensing a physiological signal;
executing at least a portion of the performance test in response to the sensed physiological signal.

22. The method of claim 21 further comprising predicting a need to operate the optical sensor at a future time in response to the physiological signal.

23. The method of claim 21 further comprising determining a patient condition in response to the physiological signal and determining a baseline signal for the optical sensor corresponding to the patient condition.

24. A non-transitory computer-readable medium storing a set of instructions which when implemented in an implantable medical device having an optical sensor comprising a plurality of modular assemblies, each assembly comprising at least one light emitting device co-located with at least one light detecting device cause the device to:
execute an optical sensor performance test;
select at least one of the plurality of assemblies to operate as a light emitting assembly in response to a result of the performance test; and
select at least one other of the plurality of optical sensor assemblies to operate as a light detecting assembly in response to the result of the performance test.

* * * * *